United States Patent [19]

Fanelli et al.

[11] Patent Number: 4,675,465

[45] Date of Patent: Jun. 23, 1987

[54] DEHYDROGENATION REACTION EMPLOYING HYDRIDE FORMING METALS, ALLOYS AND INTERMETALLIC COMPOUNDS

[75] Inventors: Anthony J. Fanelli, Rockaway; Arnulf J. Maeland, Succasunna; Robert W. Armbrust, Morris Plains; George Rak, Pine Brook, all of N.J.

[73] Assignee: Allied Corporation, Morris Township, Morris County, N.J.

[21] Appl. No.: 814,440

[22] Filed: Dec. 30, 1985

[51] Int. Cl.$^4$ ............................................. C07C 5/42
[52] U.S. Cl. ................................... 585/654; 585/617; 585/627; 585/656; 585/660
[58] Field of Search ............... 585/617, 627, 654, 656, 585/660, 616

[56] References Cited

U.S. PATENT DOCUMENTS

| 2,743,683 | 7/1973 | Croce et al. | 585/658 |
| 3,009,871 | 11/1981 | Komarewsky | 585/656 |
| 3,218,368 | 11/1965 | Neale | 585/658 |
| 3,716,496 | 2/1973 | Yoshino et al. | 585/629 |
| 4,148,833 | 4/1979 | Antos | 585/660 |
| 4,198,536 | 4/1980 | Aliev et al. | 585/658 |
| 4,497,971 | 2/1985 | Eastman et al. | 585/658 |

OTHER PUBLICATIONS

G. G. Libowitz, "Metal Hydrides for Energy Storage", Critical Materials Problems in Energy Production, Academic Press, New York, 1976, Chapter 28.

J. J. Reilly et al., "Hydrogen Storage in Metal Hydrides", *Scientific American,* 1980, 242, pp. 118-130.

R. L. Cohen et al., "Hydrogen Storage Materials: Properties and Possibilities", *Science,* 1981, vol. 214, pp. 1081-1087.

G. D. Sandrock et al., "How Metals Store Hydrogen", *Chem. Tech.,* 1981, pp. 755-762.

T. Takeshita et al., "Rare Earth Intermetallics as Synthetic Ammonia Catalysts", *J. Catal.,* 1976, vol. 44, pp. 236-243.

T. Imamoto et al., "Reduction of Organic Compounds with Rare Earth Intermetallic Compounds Containing Absorbed Hydrogen", *J. Chem. Soc. Chem. Commun.,* 1984, pp. 163-164.

K. Saga et al., "Hydrogenation of Ethylene Over LaNi$_5$ Alloy", *J. Phys. Chem.,* 1977, vol. 81, pp. 1762-1766.

K. Saga et al., *Org. Mater.* (USSR), 1978, vol. 14, p. 9.

*Primary Examiner*—Asok Pal
*Attorney, Agent, or Firm*—Ernest D. Buff; Gus T. Hampilos; Gerhard H. Fuchs

[57] ABSTRACT

A process using hydrogen dissolving metals, alloys and intermetallic compounds to drive otherwise thermodynamically unfavorable dehydrogenation reactions is disclosed. The process comprises the steps of selecting an organic reactant comprising carbon and hydrogen, and exposing the organic reactant to a material at a temperature and pressure sufficient to remove at least one hydrogen from one said organic reactant and to form a material hydride, the material being selected from the group of metals, alloys and intermetallic compounds having a negative standard free energy of formation for a hydrided product MH$_y$, where M is the material, H is hydrogen and y is a non-zero number between 0 and about 4 and represents the total hydrogen to material atom ratio wherein the standard free energy change for the reaction of the organic rectant in the present of the material to remove at least one hydrogen atom therefrom and from the material hydride is negative.

7 Claims, 2 Drawing Figures

DEHYDROGENATION REACTION EMPLOYING HYDRIDE FORMING METALS, ALLOYS AND INTERMETALLIC COMPOUNDS

FIELD OF THE INVENTION

This invention is directed to the use of hydrogen dissolving metals, alloys and intermetallic compounds to drive otherwise thermodynamically unfavorable dehydrogenation reactions.

BACKGROUND OF THE INVENTION

Metals, metal alloys and intermetallic compounds having the ability to dissolve large amounts of hydrogen are unique materials with properties of great potential value. The use of these materials as hydrogen storage media has long been recognized and much research to date has been directed towards development of these materials as storage materials; see, in particular, G. G. Libowitz "Metal Hydrides for Energy Storage," *Critical Materials Problems in Energy Production*, Academic Press, New York, 1976, Chapter 28; J. J. Reilly et al., *Scientific American* 1980, 242, p. 118; R. L. Cohen et al., *Science*, 1981, 1081, p. 214; and G. D. Sandrock et al., *Chem. Tech.*, 1981, p. 754.

The chemical use of these materials has received much less attention. However, since hydrogen is involved in many industrial chemical and petrochemical processes, some exploration of these unique materials in such applications has been undertaken. In particular, chemical applications including the use of hydrogen dissolving metals and alloys in catalytic hydrogenation reactions have been reported by T. Takeshita et al., *J. Catal.*, 1976, Vol. 44, p. 236, T. Imomoto et al., *J. Chem. Soc., Chem. Commun.*, 1984, p. 163; K. Saga et al., *J. Phys. Chem.*, 1977, Vol. 81, p. 1762, and in *Org. Mater.* (USSR), 1978, Vol. 14, p. 9.

Dehydrogenation reactions, for example the conversion of an alkane to an alkene, are thermodynamically unfavorable at moderate temperatures. To obtain high conversions, high temperatures must be used; alternatively, the reaction may be thermodynamically driven at moderate temperatures by the use of oxygen in the reaction mixture. However, both of these measures give rise to unwanted and wasteful side reactions. In the former case, high temperatures in excess of 700° C. can give rise to unwanted coking, cracking and isomerization reactions. In the later case, oxygen is often employed to drive the reactions through the formation of water. However, the use of oxygen can result in combustion reactions causing the conversion of hydrocarbons to carbon oxides. Thus, the need exists for the development of a low temperature dehydrogenation process to obtain high yields of hydrogenated products which avoids the occurrence of the above-noted side reactions which cause the loss of valuable reagents.

BRIEF DESCRIPTION OF THE INVENTION

We have discovered a process for dehydrogenating chemical reactants at lower temperatures and under conditions which substantially reduce side reactions and the loss of valuable reagents. In particular, the process is directed to the dehydrogenation of hydrocarbons (i.e., organic reactants comprising carbon and hydrogen) and comprises the steps of:

(a) selecting an organic reactant comprising carbon and hydrogen; and (b) exposing the organic reactant to a hydridable material at a temperature and pressure sufficient to remove at least one hydrogen atom from said organic reactants and form a material hydride therefrom, the material being selected from the group of metals, alloys, intermetallic compounds and mixtures thereof having a negative standard free energy of formation for the material hydride $MH_y$, where M is the material, H is hydrogen, and y is a non-zero number between 0 and about 4 and represents the hydrogen to total material atom ratio, and the standard free energy change for the reaction of the organic reactant in the presence of the material to remove at least one hydrogen atom therefrom and form the material hydride is negative.

DETAILED DESCRIPTION OF THE INVENTION

Figure 1:
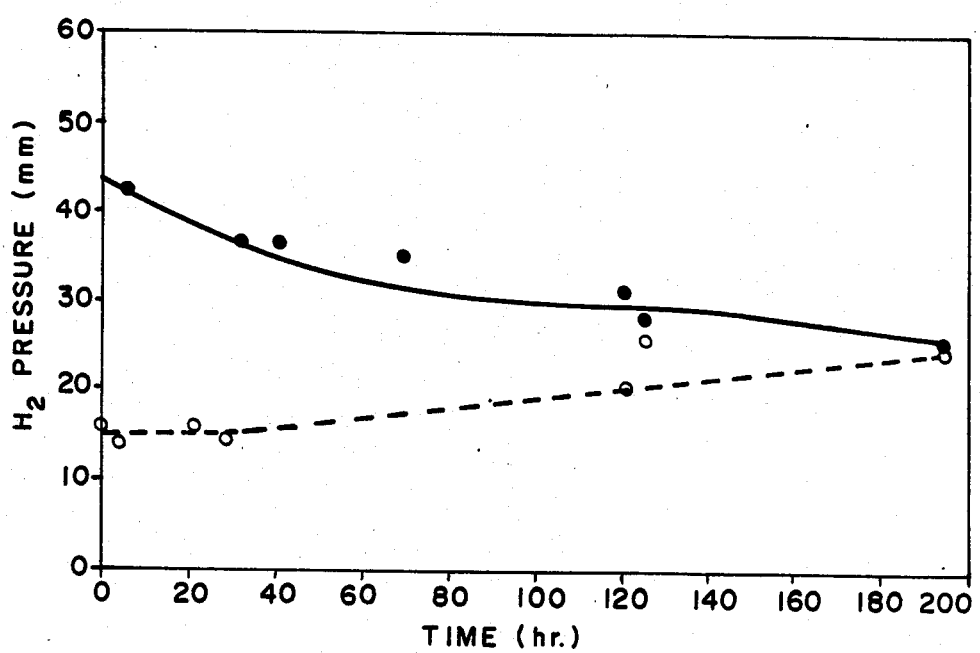
FIG. 1 is a graph of the amount of hydrogen observed during the dehydrogenation reaction vs. the amount expected for $i\text{-}C_4H_{10}$ without titanium present.

The present invention is directed to the use of hydrogen dissolving metals, alloys or intermetallic compounds to drive an otherwise thermodynamically unfavorable reaction. More particularly, the invention is directed to the use of these hydrogen dissolving (hydridable) materials to drive dehydrogenation reactions which are thermodynamically unfavorable at moderate temperatures. The useful metals, alloys and intermetallic compounds which dissolve hydrogen are selected from those materials which exhibit a negative free energy on hydride formation. More importantly, the materials useful in the present invention are those hydride forming materials which yield a negative free energy of reaction for the dehydrogenation reaction. The advantages of the use of these hydrides includes a reduction in the reaction temperature and the avoidance of side reactions and the loss of valuable reactants which can occur when employing high temperatures or oxygen to carry out a dehydrogenation process.

The dehydrogenation reactions of the present invention can be expressed by a number of formulae including, for example, $$C_nH_{n+x} + M \rightarrow C_nH_{n+x-y} + MH_y \qquad (1)$$

where $0 < x \leq n+2$, where $0 < y \leq 2$, where $y \leq x$, and where $n \geq 2$. Equation (1) describes reactions which include the dehydrogenation of alkanes to alkenes, alkynes, dienes or diynes, alkenes to dienes, alkynes or diynes, and alkynes to diynes employing monohydride- or dihydride-forming materials. Other reactions within the scope of the invention include the formation of aldehydes and ketones from alcohols (e.g., formaldehyde from methanol), as well as the formation of unsaturated molecules containing heteroatom functional groups such as vinyl or unsaturated ethers, unsaturated alcohols, carboxylic acids and unsaturated halogenated hydrocarbons. These latter examples are derived from the parent functionalized saturated hydrocarbon; for example, vinyl chloride derived from chloroethane. To dehydrogenate the hydrocarbon at moderate temperatures in the presence of the material M, the thermodynamics of the reaction must be such that the standard free energy of the reaction is negative. The more negative the free energy, the more favorable the reaction; i.e., the lower the temperature necessary to cause the reaction to occur.

The hydridable materials M useful in the reactions include those materials selected from the group of metals, alloys, intermetallic compounds and mixtures thereof which exhibit a negative standard (25° C.) free energy of formation (i.e., the $\Delta G^{0-} < 0$ kcal/mol) for the product $MH_y$, wherein H is hydrogen and y is a non-zero number between 0 and about 4 and represents the hydrogen to total material atom ratio. Examples of materials which exhibit a negative free energy upon forming the hydride include:

(a) Ti, where $Ti + H_2 \rightarrow TiH_2$ has a $\Delta G^{0-} = -20.6$ kcal/mole at 25° C.;

(b) Zr, where $Zr + H_2 \rightarrow ZrH_2$ has a $\Delta G^{0-} = -29.3$ kcal/mole at 25° C.;

(c) $V_{0.603}Ti_{0.297}Fe_{0.02}H$, where $2V_{0.603}Ti_{0.297}Fe_{0.02}H + H_2 \rightarrow 2V_{0.603}Ti_{0.297}Fe_{0.02}H_2$ has a $\Delta G^{0-} = -1.8$ kcal/mol;

(d) $V_{0.735}Ti_{0.245}Fe_{0.02}H$, where $2V_{0.735}Ti_{0.245}Fe_{0.02}H + H_2 \rightarrow 2V_{0.735}Ti_{0.245}Fe_{0.02}H_2$ has a $\Delta G^{0-} = -4.3$ kcal/mol;

(e) Yb, where $Yb + H_2 \rightarrow YbH_2$ has a $\Delta G^{0-} = -33.3$ kcal/mol;

(f) U, where $2U + 3H_2 2UH_3$ has $\Delta G^{0-} = -11.6$ kcal/mol;

(g) Gd, where $Gd + H_2 \rightarrow GdH_2$ has a $\Delta G^{0-} = -37.5$ kcal/mol;

(h) $CaNi_5$, where $2CaNi_5 + 5H_2 \rightarrow 2CaNi_5H_5$ has a $\Delta G^{0-} = -3.5$ kcal/mol;

(i) $GdNi_2$, where $2GdNi_2 + 5H_2 \rightarrow 2GdNi_2H_5$ has a $\Delta G^{0-} = -10.5$ k/cal/mole;

(j) ZrCo, where $2ZrCo + H_2 \rightarrow 2ZrCoH$ has a $\Delta G^{0-} = -27$ kcal/mol;

(k) Hf, where $2Hf + H_2 \rightarrow 2HfH$ has a $\Delta G^{0-} = -23$ kcal/mol; and, (l) $Zr_{0.55}Ti_{0.45}$, where $2Zr_{0.55}Ti_{0.45} + H_2 \rightarrow 2Zr_{0.55}Ti_{0.45}H$ has a $\Delta G^{0-} = -27$ kcal/mol.

As stated above, the standard free energy change for the dehydrogenation reaction must be negative in order to be favorable at moderate temperatures. Thus, for the reaction illustrated in equation (1) to be thermodynamically favorable at moderate temperatures, the free energy of formation of $MH_y$ from M and $H_2$ must be sufficiently negative to more than counterbalance the free energy of the reaction $$C_nH_{n+x} \rightarrow C_nH_{n+x-y} + H_y \qquad (2)$$

In general, the dehydrogenation reactions of the present invention can be carried out at a temperature between about 175° C. and about 500° C. under a pressure between about 15 psia and about 800 psia. Preferably, the reactions are carried out at a temperature between about 175° C. and about 400° C. under a pressure between about 200 psia and about 500 psia. While the most preferred temperature and pressure may be different for each set of reactants, those of ordinary skill in this art can readily determine the preferred temperature and pressure from the thermodynamic considerations discussed above and known dyhdrogenation reaction conditions.

An additional important aspect of the invention is the regeneration of the hydridable material employed in the dehydrogenation process. This step is accomplished by decomposing the material hydride at elevated temperatures and/or reduced pressures. By choosing a hydridable material having a negative free energy sufficient to yield a dehydrogenation reaction having a negative free energy, but not so negative as to require an inordinantly high temperature and/or low pressure to decompose the hydride formed from the hydrogenation reaction, a cyclic process can result. Moreover, the recovered hydrogen from the decomposition step can be employed in subsequent reactions, e.g., hydrogenation reactions. Therefore, it is preferred to choose hydridable materials having a free energy of formation of the hydride between about $-20$ and about $-30$ kcal/mol, with the most preferred hydridable materials being those having a free energy of formations of the hydride between about $-20$ and about $-30$ kcal/mol.

As an example of the process, isobutane was converted into isobutene in the presence of titanium according to the following formula:

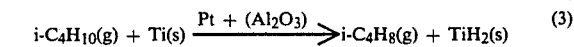

$$i\text{-}C_4H_{10}(g) + Ti(s) \xrightarrow{Pt + (Al_2O_3)} i\text{-}C_4H_8(g) + TiH_2(s) \qquad (3)$$

This dehydrogenation reaction was carried out in a 1.27 cm outer diameter stainless steel tubular reactor shaped in the form of a "U". The catalyst employed in the reaction was a mixture of 2.25 grams of $Pt/Al_2O_3$ catalyst (5 wt % Pt, Englehardt 14772). The catalyst was supported on a stainless steel porous disk which was welded into one of the arms of the reactor. The reaction temperature was monitored by a thermocouple inserted into the reactor. Hydrocarbons were passed through a silica gel-molecular sieve dryer and oxygen trap before entering the reactor. The effluent from the reactor was fed directly into a gas chromatograph. Hydrocarbon products from the isobutane reaction were analyzed by means of a Durapac on Poracel C (Supelco) column in series with a Carbopack/0.19% picric acid (Supelco) column at 343° K. At 25° C., the free energy of formation (kcal/mol) of the reactants are as follows: $-4.99$ for $i\text{-}C_4H_{10}(g)$, 30 13.88 for $i\text{-}C_4H_8(g)$, and $-20.6$ for $TiH_2$. Thus, the standard free energy changes ($\Delta G^{0-}$) for Equation (3) is $-1.7$ kcal/mole at 25° C.

The theoretical $i\text{-}C_4H_{10}:i\text{-}C_4H_8$ equilibrium ratio, without removal of hydrogen, is 19:1 (5.3 percent conversion) at 641° K. and 101.3 kPa pressure. An initial enhancement of isobutene above the theoretical value was achieved at 641° K. and 90 $h^{-1}$ space velocity over a mixture of 2.25 g $Pt/Al_2O_3$ catalyst and 3.48 grams titanium. Two cycles were carried out. In the first cycle, a ratio of 12.5:1 (7.4 percent conversion) was initially observed, the ratio increasing toward the theoretical 19:1 as the titanium became saturated with hydrogen. Thereafter, the titanium was regenerated by removing the hydrogen at 873° K. and 0.1 Pa pressure. Following the regeneration of the titanium, an initial $i\text{-}C_4H_{10}:i\text{-}C_4H_8$ ratio of 8.6:1 (10.4 percent conversion) was observed, which again increased toward 19:1 as the titanium became saturated with hydrogen. Quite clearly, the presence of the hydridable material, titanium, enhanced the conversion from alkane to alkene by 40% or more over theoretical.

Generally, hydrogen is never completely removed from the reaction mixture, its concentration increasing with time as the hydridable material capacity becomes exhausted. Thus, the amount of hydrogen in the reactor effluent varies inversely with the dehydrogenated product produced, a result opposite to that expected in the absence of hydride formation. The amount of hydrogen observed vs. the amount expected, for i-$C_4H_{10}$ without titanium present, is plotted in FIG. 1. The difference in the two curves represents the amount of hydrogen absorbed by the titanium. The hydrogen recovered during the hydridable material regeneration process step can be measured to determine the composition of the hydride formed. In this example, the hydride product corresponded to TiH as the composition of the titanium hydride produced.

Figure 2:
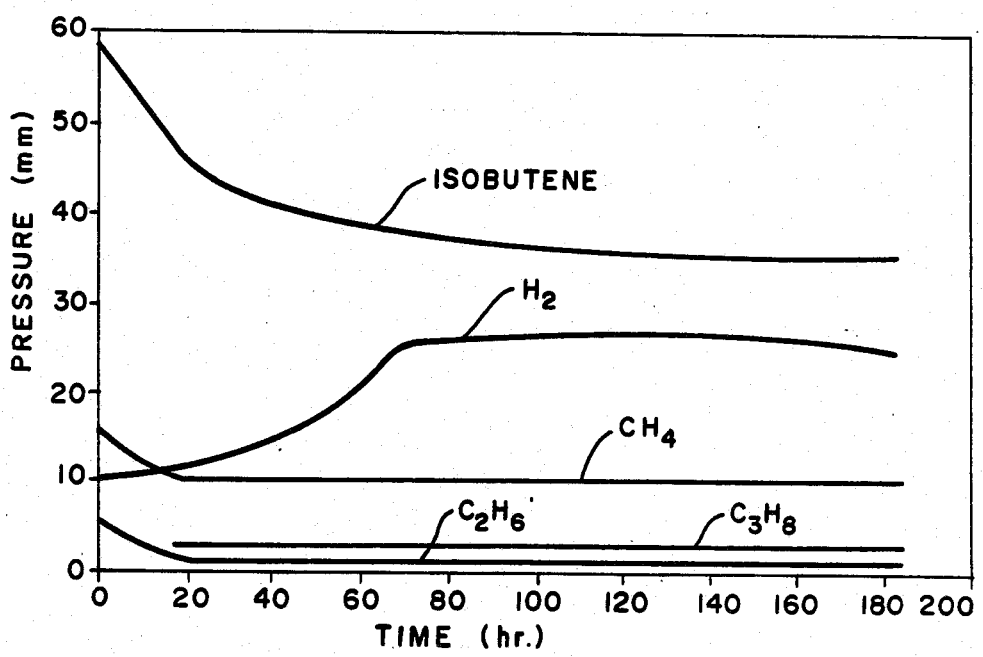
FIG. 2 is a time profile of the production of hydrogenalysis products and isomerization products for the conversion of $i\text{-}C_4H_{10}$ to $i\text{-}C_4H_8$.

Some hydrogenalysis ($CH_4$, $C_2H_6$, $C_3H_8$) and isomerization (n-$C_4H_{10}$) products, as expected for a i-$C_4H_{10} \rightarrow$ i-$C_4H_8$ in the presence of a platinum/alumina catalyst, were observed in addition to the isobutene. However, following an initial surge, the hydrogenalysis products quickly level out when a hydridable material is employed to concentrations remaining independent is time. The time profiles of the various products are illustrated in FIG. 2. This effect would not occur in the absence of the hydridable material.

The addition of the hydride-forming material to the reactants also significantly increases the selectivity of the products. For example, selectivity of i-$C_4H_8$:i-$C_4H_{10}$ (platinum alumina catalyst) in the presence of a hydridable material ($Ti_{0.63}V_{0.27}Fe_{0.1}$) was 15; in the absence of this hydridable intermetallic compound, the selectivity ratio of i-$C_4H_8$:i-$C_4H_{10}$ was 5.

Having thus described the invention in rather full detail it will be understood that these details need not be strictly adhered to but that various changes, modifications, additions or deletions may suggest themself to one skilled in the art, all of which would fall within the scope of the invention as defined by the subjoined claims effecting the scope of the invention.

We claim:

1. A process for dehydrogenating reactants which comprises the steps of:
   (a) selecting a reactant comprising a hydrocarbon; and
   (b) exposing the reactant to a material at a temperature and pressure sufficient to remove at least one hydrogen atom from said hydrocarbon and form at the temperature and pressure of exposure a material hydride the material being selected from the group of metals, alloys and intermetallic compounds having a negative free energy of formation for a hydrided product $MH_y$, where M is the material, H is hydrogen and y is a non-zero number between 0 to 4 and represents the total hydrogen to material atom ratio, at the temperature and pressure of exposure, and wherein the standard free energy change for the reaction of the hydrocarbon in the presence of the material to remove at least one hydrogen atom therefrom and form the material hydride is negative.

2. The process of claim 1 wherein the reaction of the hydrocarbon in the presence of the material is represented by the formula $C_nH_{n+x} + M \rightarrow C_nH_{n+x-y} + MH_y$, where $0 < x \leq n+2$, where $0 < y \leq 2$, where $y \leq x$, and where $n \geq 2$.

3. The process of claim 1 wherein the reactant is selected from the group of alkanes and alkenes.

4. The process of claim 1 further comprising the steps of removing the exposed reactant from the reaction, heating the material hydride under a pressure sufficient to regenerate at least a portion of the material, and exposing a second reactant comprising a hydrocarbon to the regenerated material.

5. The process of claim 4 wherein the second reactant has the same composition as the exposed reactant.

6. The process of claim 4 wherein the $\Delta G^{0-}$ of formation of a hydrided material from the material is between about $-20$ kcal/mol and about $-30$ kcal/mol.

7. The process of claim 4 wherein the $\Delta G^{0-}$ of formation of a hydrided material from the material is between about $-5$ kcal/mol and about $-30$ kcal/mol.

* * * * *